United States Patent [19]

Barns et al.

[11] Patent Number: 5,217,862

[45] Date of Patent: Jun. 8, 1993

[54] **METHOD FOR THE DETECTION OF *NEISSERIA GONORRHOEAE***

[75] Inventors: Susan M. Barns, Hopkinton; Donald N. Halbert; David J. Lane, both of Milford, all of Mass.

[73] Assignee: Amoco Corporation, Chicago, Ill.

[21] Appl. No.: 775,210

[22] Filed: Oct. 11, 1991

Related U.S. Application Data

[63] Continuation of Ser. No. 356,155, May 24, 1989, abandoned.

[51] Int. Cl.$^5$ .......................... C12Q 1/68; C12Q 1/02; G01N 33/566; G07H 15/12
[52] U.S. Cl. .......................................... 435/6; 435/29; 435/34; 436/501; 436/94; 536/24.32; 935/77; 935/78
[58] Field of Search ...................... 435/6, 822, 871, 29; 536/27; 935/77, 78; 436/501, 94

[56] References Cited

U.S. PATENT DOCUMENTS 4,900,659  2/1990  Lo et al.

FOREIGN PATENT DOCUMENTS

| | | |
|---|---|---|
| 0237737 | 9/1987 | European Pat. Off. ............. 435/6 |
| 0294595 | 12/1988 | European Pat. Off. ............. 435/6 |
| 0337896 | 10/1989 | European Pat. Off. ............. 435/6 |
| 0353985 | 2/1990 | European Pat. Off. ............. 435/6 |
| 8803957 | 6/1988 | PCT Int'l Appl. ................. 435/6 |

OTHER PUBLICATIONS

Harper et al., Abstracts of the Annual Meeting, p. 337, C-35. Ann. Mtg. Amer. Soc. for Microbiol., Miami Beach, Fla., May 8-13, 1988.
Dialog Information Services, File 154, Medline 83-90, Dialog accession No. 06979511, Donegan J. J. et al: "Isolation of a species-specific DNA probe for *Neisseria gonorrhoeae* using a novel technique particularly suitable for use with closely related species displaying high levels of DNA homology", Mol Cell Probes (England) Mar. 1989, 3 (1) pp. 13-26.
Bergey's Manual of Systematic Bacteriology (N. R. Krieg [ed.], 1984, pp. 288-296, Williams and Wilkins.
Totten et al. (The Journal of Infectious Diseases, 1983, 148:462-471).
Pace and Campbell (Journal of Bacteriology 107:543-547, 1971).
Welcher et al. (Nucleic Acids Research, 1986, 14:10027-10044).
Kohne et al. (Biophysical Journal 8:1104-1118, 1968).
Sogin, Sogin and Woese (Journal of Milecular Evolution 1:173-184, 1972).
Fox, Pechman and Woese (International Journal of Systematic Bacteriology 27:44-57, 1977).
Lo and Yang et al. European Patent Application No. 87101215.9.
N.V. Innogenetics S.A. European Patent Application 89401045.3.

Primary Examiner—Margaret Moskowitz
Assistant Examiner—Stephanie W. Zitomer
Attorney, Agent, or Firm—Norval B. Galloway

[57] ABSTRACT

Nucleic acid probes capable of hybridizing to rRNA sequences of *Neisseria gonorrhoeae* and not to rRNA sequences of non-*Neisseria gonorrhoeae* are described along with methods utilizing such probes for the detection of *Neisseria gonorrhoeae* in clinical and other samples.

8 Claims, No Drawings

METHOD FOR THE DETECTION OF *NEISSERIA GONORRHOEAE*

This is a continuation of application Ser. No. 07/356,155, filed May 24, 1989, now abandoned.

FIELD OF THE INVENTION

This invention relates to detecting bacteria belonging to the genus Neisseria and more specifically provides nucleic acid probes and compositions along with methods for their use for the specific detection of *Neisseria gonorrhoeae*.

BACKGROUND OF THE INVENTION

The term "*Neisseria gonorrhoeae*" as used herein, refers to the bacteria classified as such in Bergey's Manual of Systematic Bacteriology (N. R. Krieg [ed.], 1984, pp. 288-296, Williams and Wilkins). Detection of *Neisseria gonorrhoeae* is important in various medical and public health contexts. *Neisseria gonorrhoeae* is one of the leading causes of epidemic sexually transmitted disease, with approximately one million cases reported in the United States in 1983. Infection with this pathogen can result in a wide variety of clinical manifestations, most commonly urethritis, cervicitis and proctitis. However, infection frequently results in diseases requiring hospitalization, such as endometritis, salpingitis and pelvic inflammatory disease.

Therefore, it is an aspect of the present invention to provide nucleic acid probes for use in a hybridization assay system capable of rapidly detecting *Neisseria gonorrhoeae* and which is generally applicable to all types of clinical samples.

The scope and severity of disease caused by this organism have resulted in the development of a variety of methods for detection from clinical samples, however, the only methods currently recommended by the Center for Disease Control, the Public Health Association or the American Society for Microbiology for detection of this organism from male or female specimens rely primarily on culture.

Highest culture recovery of viable organisms requires immediate plating of a freshly collected specimen on an appropriate selective culture medium (e.g. Thayer-Martin medium) and growth in a reduced oxygen atmosphere (3-10% $CO_2$) at 35° C. If immediate plating is not possible, then a non-nutritive transport system can be used, as long as the sample is held for less than six hours. If the sample cannot be plated within six hours, then a nutritive transport system can be employed, containing growth media and a source of $CO_2$. Following plating on selective media, cultures are incubated at 34°-36° C. in a 3%-10% $CO_2$ environment for 28-48 hours. Colonies suspected of being Neisseria then are Gram-stained and tested for oxidase activity. Oxidase positive, Gram-negative diplococci are indicative of Neisseria spp. and must then be confirmed as *Neisseria gonorrhoeae*, since the culture sites may contain a variety of non-pathogenic Neisseria. Confirmation can be carried out in a variety of ways, most commonly by carbohydrate utilization, latex agglutination or immunofluorescence tests. However, any of these confirmatory tests are labor intensive and time consuming, often requiring additional incubation and/or growth periods.

It is another aspect of the present invention to avoid the disadvantages associated with traditional culturing techniques.

An enzyme immunoassay for identification of *Neisseria gonorrhoeae* directly from clinical specimens (Gonozyme TM, Abbot Laboratories, Chicago, IL) has been available for several years, however, a variety of clinical studies have indicated that this test suffers from a lack of sensitivity and specificity. The assay also requires 3-4 hours to perform, and requires the purchase of specific signal detection equipment.

It is yet another aspect of the present invention to avoid the disadvantages associated with enzyme immunoassays and to employ nucleic acid probes to detect *Neisseria gonorrhoeae*.

It is still another aspect to provide nucleic acid probes and hybridization techniques are described which permit the specific detection of *Neisseria gonorrhoeae* in clinical specimens.

As used herein, probe(s) refer to synthetic or biologically produced nucleic acids (DNA or RNA) which, by design or selection, contain specific nucleotide sequences that allow them to hybridize under defined predetermined stringencies, specifically (i.e., preferentially, see below—Hybridization) to target nucleic acid sequences.

Hybridization traditionally is understood as the process by which, under predetermined reaction conditions, two partially or completely complementary strands of nucleic acid are allowed to come together in an antiparallel fashion to form a double-stranded nucleic acid with specific and stable hydrogen bonds.

Totten et al. (The Journal of Infectious Diseases, 1983, 148:462-471) describe detection of *Neisseria gonorrhoeae* in clinical specimens by utilizing DNA probes directed against the so-called cryptic plasmid which commonly is associated with this bacterium. However, it is well known that the presence of this plasmid in *Neisseria gonorrhoeae* isolates is highly regional (occurring in from 78% to 98% of isolates in different parts of the United States), predicting a high degree of variability in any assay based on the detection of its presence in test samples.

It is yet another aspect of the present invention to remove this source of variability by providing probes which hybridize to nucleic acid sequences that are common to all strains of *Neisseria gonorrhoeae*, but which do not hybridize to any commensal non-*Neisseria gonorrhoeae* or other flora that may be present in test samples.

Lo and Yang et al. (European Patent Application 87101215.9) describe the isolation of nucleic acid probes directed against chromosomal genes of *Neisseria gonorrhoeae*. These probes are purported to specifically recognize six strains of *Neisseria gonorrhoeae*, with no cross-hybridization to six strains of *Neisseria meningitidis*. Welcher et al. (Nucleic Acids Research, 1986, 14:10027-10044), also describe the isolation of chromosomally-targeted DNA probes. These probes are purported to specifically recognize the strain from which they were selected as well as six clinical isolates of *Neisseria gonorrhoeae*, with no cross-hybridization to 7 other Neisseria spp., *E. coli* or the commensal bacterium *Branhamella catarrhalis*. However, testing of the aforementioned probes against a wide variety of organisms was not reported. Also, because the chromosomal target sequences are represented in low copy number in each cell, the described assays are not very sensitive and, as a consequence, their utility is significantly restricted in clinical applications.

It is yet another aspect of the present invention to provide nucleic acid probes which combine high specificity for *Neisseria gonorrhoeae* with high sensitivity by the utilization of probes which hybridize to ribosomal RNA molecules which are present in high abundance in the target bacteria.

Ribosomes are of profound importance to all organisms because they serve as the only known means of translating genetic information into cellular proteins, the main structural and catalytic elements of life. A clear manifestation of this importance is the observation that all cells have ribosomes.

Ribosomes contain three distinct RNA molecules which, at least in *E. coli*, are referred to as 5S, 16S and 23S rRNAs. These names historically are related to the size of the RNA molecules, as determined by their sedimentation rate. In actuality, however, ribosomal RNA molecules vary somewhat in size between organisms. Nonetheless, 5S, 16S, and 23S rRNA are commonly used as generic names for the homologous RNA molecules in any bacterium, and this convention will be continued herein.

While Kohne et al. (Biophysical Journal 8:1104–1118, 1968) discuss one method for preparing probes to rRNA sequences, they do not provide the teaching necessary to make *Neisseria gonorrhoeae*-specific probes.

Pace and Campbell (Journal of Bacteriology 107:543–547, 1971) discuss the homology of ribosomal ribonucleic acids from diverse bacterial species and a hybridization method for quantifying such homology levels. Similarly, Sogin, Sogin and Woese (Journal of Molecular Evolution 1:173–184, 1972) discuss the theoretical and practical aspects of using primary structural characterization of different ribosomal RNA molecules for evaluating phylogenetic relationships. Fox, Pechman and Woese (International Journal of Systematic Bacteriology 27:44–57, 1977) discuss the comparative cataloging of 16S ribosomal RNAs as an approach to prokaryotic systematics. These references, however, fail to relieve the deficiency of Kohne's teaching with respect to *Neisseria gonorrhoeae* and, in particular, do not provide *Neisseria gonorrhoeae*-specific probes useful in assays for detecting *Neisseria gonorrhoeae* in clinical samples.

Hogan et al. (European patent publication WO 88/03957) describe a number of probes which are claimed to be specific for *Neisseria gonorrhoeae* rRNA. However, Hogan et al. only demonstrate that their probes hybridize to the *Neisseria gonorrhoeae* strain against which they are designed-a foregone, and hardly novel, conclusion. No data is given to suggest that any of the probes will hybridize to additional *N. gonorrhoeae* strains. Similarly, the specificity of the probes is defined by lack of hybridization to only single strains of a few (8) related Neisseria species. No data is provided to indicate which, if any, of the probes have the claimed specifity, i.e. that they are inclusive for all or even most *N. gonorrhoeae*.

It is another aspect of the present invention to provide nucleic acid probes that are well characterized with respect to their hybridization behavior toward Neisseria and non-Neisseria bacteria.

Ribosomal RNAs are highly structured molecules. This structure depends largely on the same types of interactions which govern probe-target interactions. Therefore, not all potentially useful hybridization target sequences are equally accessible to probes under every conceivable assay condition.

It is yet another aspect of the present invention to provide probes and probe sets which can hybridize to rRNA target regions which can be rendered accessible to probes under normal assay conditions.

The stringency of a particular set of hybridization conditions is defined by the length and base composition of the probe/target duplex, as well as by the level and geometry of mispairing between the two nucleic acids.

Stringency may also be governed by such reaction parameters as the concentration and type of ionic species present in the hybridization solution, the types and concentrations of denaturing agents present, and/or the temperature of hybridization. Generally, as hybridization conditions become more stringent, longer probes are preferred if stable hybrids are to be formed. As a corollary, the stringency of the conditions under which a hybridization is to take place (e.g., based on the type of assay to be performed) will dictate certain characteristics of the preferred probes to be employed. Such relationships are well understood and can be readily manipulated by those skilled in the art.

As a general matter, dependent upon probe length, such persons understand stringent conditions to mean approximately 35° C.–65° C. in a salt solution of approximately 0.9 molar.

SUMMARY OF THE INVENTION

In accordance with the various principles and aspects of the present invention, there are provided nucleic acid probes and probe sets comprising DNA or RNA sequences which hybridize, under specific conditions, to the ribosomal RNA molecules (rRNA) or rRNA genes (rDNA) of *Neisseria gonorrhoeae* but which do not hybridize, under the same conditions, to the rRNA or rDNA of other related bacteria which may be present in test samples. Therefore the probe(s) of the present invention.provide the basis for development of a valuable nucleic acid hybridization assay for the specific detection of *N. gonorrhoeae* in clinical or environmental samples.

In our experience such nucleic acid hybridization-based assays have been discovered to impart enhanced performance capabilities with respect to most currently available microbiological methods for detection of bacteria in test samples, generally including:

a) increased sensitivity; i.e., the ability to detect said fewer bacteria in a given sample;

b) potentially significant reductions in assay cost due to the use of inexpensive reagents and reduced labor;

c) accurate identification of even biochemically unusual strains of the target bacteria;

d) faster results because such tests do not require the isolation of the target bacterium from the sample prior to testing.

It has been discovered that other advantages incurred by directing the probes of the present invention against rRNA include the fact that the rRNAs detected constitute a significant component of cellular mass. Although estimates of cellular ribosome content vary, actively growing *Neisseria gonorrhoeae* may contain upwards of 20,000 ribosomes per cell, and therefore 20,000 copies of each of the rRNAs. In contrast, other potential cellular target molecules such as genes or RNA transcripts thereof, are less ideal since they are present in much lower abundance.

A further unexpected advantage is that the rRNAs (and the genes specifying them) appear not to be subject to lateral transfer between contemporary organisms. Thus, the rRNA primary structure provides an organism-specific molecular target, rather than a gene-specific target as would likely be the case, for example of a plasmid-borne gene or product thereof which may be subject to lateral transmission between contemporary organisms.

Additionally, the present invention provides a number of probes and probe sets to *Neisseria gonorrhoeae* rRNA target sequences which are sufficiently similar in all *Neisseria gonorrhoeae* strains tested that they can hybridize to the target region in all such *Neisseria gonorrhoeae*. Advantageously, these same rRNA target sequences are sufficiently different in most non-*Neisseria gonorrhoeae* rRNAs that, under conditions where these probes hybridizes to *N. gonorrhoeae* rRNAs they do not hybridize to most non-*N. gonorrhoeae* rRNAs. These probe characteristics are defined as inclusivity and exclusivity, respectively.

Other probes of the present invention are fully inclusive for *N. gonorrhoeae* strains, but do also hybridize to at least some non-*N. gonorrhoeae* target rRNAs. They are intended to be used as part of probe sets which also contain one or more of the aforementioned *N. gonorrhoeae*-specific probes and are designed to enhance the hybridization behavior of said *N. gonorrhoeae*-specific probes by, for example, acting as signal-carrying probes (detection probes) and/or by enhancing the accessability of the target site of the *N. gonorrhoeae*-specific probe.

The discovery that probes could be generated with the extraordinary inclusivity and exclusivity characteristics of those of the present invention with respect to *N. gonorrhoeae* was unpredictable and unexpected.

In addition to their hybridization properties, the probes of the present invention also may contain certain constituents that improve their proper or optimal functioning under particular assay conditions. For example, probes may be modified to improve their resistance to nuclease degradation (e.g. by end capping), to carry detection ligands (e.g. fluorescein, 32-P, biotin, etc.), or to facilitate their capture onto a solid support (e.g., poly-deoxyadenosine "tails"). Such modifications are elaborations on the basic probe function which is its ability to usefully discriminate between target and non-target organisms in a hybridization assay.

BRIEF DESCRIPTION OF THE TABLES

Further understanding of the principles and aspects of the present invention may be made by reference to the tables wherein:

Table 1—Shows a detailed alignment of the nucleotide sequences of the preferred 16S rRNA-targeted probes of the present invention with the target nucleotide sequences of a number of Neisseria strains. The corresponding portions of the 16S rRNAs from a number of closely related non-*Neisseria gonorrhoeae* bacteria also are shown for comparison. Target RNA sequences are written 5' to 3', probe sequences are DNA and written 3' to 5'. Probes are shown along with the "core" region of variation upon which their inclusivity and exclusivity behaviors are based. The lower case C (c) in probes 1116 and 1117 indicates a modified cytosine residue to which a detection ligand may or may not be attached depending on the assay format employed (see below).

Table 2—Shows a detailed alignment of the nucleotide sequences of the preferred 23S rRNA-targeted probes of the present invention with the target nucleotide sequences of *Neisseria gonorrhoeae*. The corresponding portions of the 23S rRNAs from *Escherichia coli* and *Neisseria meningitidis* also are shown for comparison. RNA (target) sequences are written 5' to 3', probe sequences are DNA and written 3' to 5'. Probes are shown along with the "core" region of variation upon which their inclusivity and exclusivity behaviors are based.

Table 3—Exemplifies the inclusivity behavior of the preferred probes toward a representative sampling of *Neisseria gonorrhoeae* strains in a dot blot hybridization assay.

Table 4—Exemplifies the exclusivity behavior of the preferred probes toward a representative sampling of non-*Neisseria gonorrhoeae* strains in a dot blot hybridization assay.

DETAILED DESCRIPTION OF THE INVENTION AND BEST MODE

Probe Development Strategy

The first step taken in the development of the probes of the present invention involved identification of regions of 16S and 23S rRNA which potentially could serve as target sites for *Neisseria gonorrhoeae*-specific nucleic acid probes. As a practical matter, it is difficult to predict, a priori, which non-*Neisseria gonorrhoeae* organisms might be present in any test sample.

Because of the large number of such potential non-*Neisseria gonorrhoeae* bacteria, demonstrating exclusivity for any given probe sequence is not only unpredictable but also extremely difficult and laborious. A more rigorous criterion was adopted which obviates the need to know what non-*Neisseria gonorrhoeae* bacteria might be present in all test samples that ultimately will be screened using the probes.

This entailed knowledge of the phylogenetic relationships among *Neisseria gonorrhoeae* and between *Neisseria gonorrhoeae* and other groups of bacteria.

Specifically, an operating but previously unproven hypothesis was adopted that if a region(s) of rRNA nucleotide sequence could be found that was different in *Neisseria gonorrhoeae* and its closest known evolutionary relative, *N. meningitidis*, then a nucleic acid probe could be constructed which would distinguish between the two in a hybridization assay. Based on phylogenetic principles, it then was extrapolated that rRNA sequences of more distantly related organisms, even though their actual identity may not necessarily be known, predictably should be as or more different in a particular region of sequence than the aforementioned close evolutionary relative of *Neisseria gonorrhoeae*. However, it cannot be predicted, a priori, whether such regions exist or if they do, where within the rRNA such regions will be located.

As the first step in identifying regions of *Neisseria gonorrhoeae* rRNA which could potentially serve as useful target sites for nucleic acid hybridization probes, relevant portions of the nucleotide sequences of the 16S and 23S rRNAs from *Neisseria gonorrhoeae*, strains ATCC19424 (the type strain) and ATCC9793 (a common clinical isolate), *Neisseria meningitidis* groups B, C and D (ATCC 13090, 13102, 13113), and *Neisseria lactamica* strain ATCC 23970 were determined.

The nucleotide sequences were determined by standard laboratory protocols either by cloning (Maniatis et al., 1982, Molecular Cloning; A Laboratory Manual, Cold Spring Harbor Laboratory, New York, pp 545) and sequencing (Maxam and Gilbert, 1977, Proceedings of the National Academy of Science, USA 74:560-564: Sanger et al., 1977, Proceedings of the National Academy of Science, USA 74:5463-5467) the genes which specify the rRNAs, and/or by direct sequencing of the rRNAs themselves using reverse transcriptase (Lane et al., 1985, Proceedings of the National Academy of Science, USA 82:6955-6959).

The determined Neisseria rRNA nucleotide sequences were compared to one another and to other available rRNA nucleotide sequences. Initial phylogenetic analysis of the sequence data indicated that the Neisseria belonged to a previously described grouping of bacteria called the Beta subdivision of the Purple Bacterial division of the eubacteria (Woese, 1987, Microbiological Reviews 51:221-271).

Comparison of the sequences of *Neisseria gonorrhoeae* and its very close relative *Neisseria meningitidis* proved especially valuable. A number of regions of 16S rRNA sequence and 23S rRNA sequence were identified which appeared to be different in the two species of Neisseria and between *Neisseria gonorrhoeae* and non-Neisseria bacteria. The location of those regions within the 16S and 23S rRNA sequences which ultimately provided the required specificity and accessability, and which are the target sites of the probes of the present invention are shown in Table 1 and 2. Also shown are more detailed comparisons of these probe target regions in a variety of Neisseria and non-Neisseria bacteria. The utility of probes based on these observed nucleotide sequence differences was confirmed by extensive dot blot hybridization testing as exemplified by the data given in Tables 3 and 4. Finally, an example of the use of multi-probe sets in a liquid hybridization assay format is described (data shown in Table 5).

PHYSICAL DESCRIPTION OF THE PROBES

The foregoing probe selection strategy yielded a number of probes useful for identifying *Neisseria gonorrhoeae* bacteria in samples. The following preferred oligonucleotide probes are disclosed herein.

16S rRNA-targeted probes

Set 1, (see Table 1a):
Probe 919: 5'-cATCGGCCGCCGATATTGGCAACGGCCTTcT-3'
Probe 1116: 5'-cCGTATTACCGCAGCTGCTGGCACGTAGTTAGCCGGTGCTTATTCTcT-3'
Probe 1117: 5'-cACAAAAGTCCTTTACAACCCGAAGGCCTTCTTCAGACACGcT-3'
Set 2, (see Table 1b):
Probe 1209: 5'-GAGGATTCCGCACATGTCAAAACCAGGT-3'
Probe 1208: 5'-cGCACCTGTGTTACGGCTCCCGAAGGCACcT-3'

23S rRNA-targeted probes

Set 3, (see Table 2a):
Probe IG700: 5'-GGACATCGCGGAATCATAGCTTTATTGC-3'
Probe IG706: 5'-CCCCGCGCTTTTCGCAGGCTTACACGTC-3'
Set 4, (see Table 2b):
Probe IG705: 5'-TTCGCTTCTCTAAGCCTATGTATTCAAC-3'
Probe 1750: 5'-TAGGATACTGCACAGAATGCAGTGGGTT-3'

Probe Set 1. Probes 919, 1116, and 1117 are targeted at three adjacent regions of the 16S rRNA (Table 1). Probe 919 is targeted at the region of *Neisseria gonorrhoeae* 16S rRNA corresponding approximately to nucleotide positions 453 to 480 (using the E. coli numbering system). A number of other versions (i.e., length variants) of probe 919 also are indicated in Table 1. Probe 1116 is targeted at positions ca. 493 to 537. Probe 1117 is targeted at positions ca. 403 to 442.

As indicated in Table 1, probe 919 is "built" around the positions of core variation which are most useful for discriminating between *Neisseria gonorrhoeae* and its very close relative, *Neisseria meningitidis*. The core sequence, CguugcCaauaucGgcggcC, in the 16S rRNA of *Neisseria gonorrhoeae* contains 4 sequence differences with respect to the homologous region of *Neisseria meningitidis* (indicated by the upper case letters in the core sequence (Table 1). Two of these four differences also are found between *N. gonorrhoeae* strains 9793 and 19424 (i.e. the U's at positions 458 and 477). However, these differences result only in G:U non-canonical pairs between probe 919 and the *N. gonorrhoeae* (strain 19424) 16S rRNA at those positions. It has been experimentally determined that probe 919 hybridizes quite efficiently to *N. gonorrhoeae* strain 19424 in spite of these G:U pairs (Table 1).

In contrast, a probe complementary to the *N. gonorrhoeae* 19424 sequence through the 919 target region hybridizes poorly to *N. gonorrhoeae* 9793 and also exhibits unacceptable levels of cross hybridization to other non-*Neisseria gonorrhoeae*, particularly *N. meningitidis*.

Also shown in Table 1 are two slighly longer versions of probe 919 (probes 1114 and 1115). These make use of the same core variation as probe 919 and exhibit similar inclusivity and exclusivity behavior as probe 919 but their extra length promotes stable probe target hybridization at higher stringencies.

Probes 1116 and 1117 do not discriminate between *Neisseria gonorrhoeae* and *Neisseria meningitidis*—as expected given the identity of the target sequences for these probes in these two bacterial 16S rRNAs (Table 1). Therefore, probes 1116 and 1117 would not be useful, on their own, as a *Neisseria gonorrhoeae*-specific probe since discrimination between these two bacteria generally is considered important for most potential applications of an assay which would employ such probes. However, probes 1116 and 1117 do have important and novel properties that make them useful when used in conjunction with probe 919 (see below).

Probe Set 2. 16S rRNA-targeted probes 1208 and 1209 also form a set (Table 1b). Probe 1209 is targeted at the region of *Neisseria gonorrhoeae* 16S rRNA corresponding to nucleotide positions 983 to 1010 (E. coli numbering). Probe 1208 is targeted at positions 1024 to 1051.

Of this set, probe 1209 is *N. gonorrhoeae*-specific, probe 1208 is designed as a helper/detection probe. Probe 1209 is built around the cytosine (C) and adenosine (A) differences found to exist between the *N. gonorrhoeae* and *N. meningitidis* 16S sequences shown in table 1. The core variation upon which the specificity of probe 1209 depends includes the region of *N. gonorrhoeae* sequence UuugacauguG. Probe 1208 does not discriminate between *N. gonorrhoeae* and *N. meningitidis*, but is useful when used in conjunction with probe 1209 in a variety of dual probe assay formats.

Probe Set 3. Probe IG700 and its helper probe IG706 form another set but are targeted at the 23S rRNA of *N. gonorrhoeae*. Of the pair, Probe IG700 is *N. gonorrhoeae*- specific. IG706 is designed as the helper/detection probe. Probe IG700 is targeted at *N. gonorrhoeae* 23S rRNA positions 89 to 116 (using the *E. coli* 23S rRNA numbering) and relies on the A and C differences shown in Table 2a. The core variation upon which the specifity of probe IG700 is based includes these positions and is defined as the *N. gonorrhoeae* sequence UaugauU (Table 2a).

Probe Set 4. Probe IG705 and its helper probe 1750 form the fourth probe set described in the present invention. Like the rest of the probe set described above, these two are targeted at adjacent regions of the *N. gonorrhoeae* rRNA. Of this pair, IG705 is *N. gonorrhoeae*-specific, probe 1750 is designed as the helper/detection probe. Probe IG705 is targeted at *N. gonorrhoeae* 23S rRNA positions 156 to 182 and relies on a single position of difference between *N. gonorrhoeae* and *N. meningitidis* (adenosine=A, Table 2b) for specifity. Probe IG705, therefore, is roughly centered about this position just as the above described *N. gonorrhoeae*-specific probes 919, 1209 and IG700 are centered around their respective regions of core variation. Probe 1750, the companion helper/detection probe of this probe set is targeted at *N. gonorrhoeae* 23S rRNA positions 126 to 154.

The specific behaviors of the probes and probe sets described above are dependent to a significant extent on the assay format in which they are employed. Conversely, the assay format will dictate certain of the optimal design features of particular probes. The "essence" of the probes of the invention is not to be construed as restricted to the specific string of nucleotides in the probes named, for example, 919 and 1116 and 1117. The length of these particular oligonucleotides was optimized for use in the dot blot assay (and certain other anticipated assays) described below. It is well known to one skilled in the art that optimal probe length will be a function of the stringency of the hybridization conditions chosen and hence the length of the instant probes may be altered in accordance therewith. Also, in considering sets comprised of more than one probe, it is desirable that all probes behave in a compatible manner in any particular format in which they are both employed. Thus, the exact length of a particular probe will to a certain extent reflect its specific intended use.

The "essence" of the probes described herein resides in the discovery and utilization of the *Neisseria gonorrhoeae*-specific sequences described above and given in Tables 1 and 2 (core variation).

Also note that because of the proximity of their target sites on the *N. gonorrhoeae* 23S rRNA, probes IG700 and IG705 (with or without the use of their individual helper probes) also form a useful probe set. Since both probes individually are specific for *N. gonorrhoeae* (with the noted exception of probe IG705 vs. *N. flava*), a dual probe assay format using one as a capture probe and the other as a detection probe would be significantly more "robust" than a specific/non-specific capture/detection probe pair.

Hybridization Analysis of Probe Behavior

The sequence data in Tables 1 and 2 suggested that probes 919, 1209, IG700 and IG705 (or variations thereof) might be useful as hybridization probes for detecting *Neisseria gonorrhoeae*. However, potentially much greater sequence variation might exist in other *Neisseria gonorrhoeae* strains not inspected by sequence analysis. Such variation might reduce or eliminate hybridization by the prospective probes to some or many untested *Neisseria gonorrhoeae* strains.

Equally as important as the inclusivity behavior of the probes, is their exclusivity behavior, i.e., their reactivity toward non-*Neisseria gonorrhoeae* bacteria. The discovery of the few small stretchs of sequence variation between the rRNAs of *Neisseria gonorrhoeae* and *Neisseria meningitidis* shown in Tables 1 and 2 was unanticipated and unexpected. However, as discussed above these patterns of sequence difference might not hold for other strains of *Neisseria meningitidis*, strains of other Neisseria species or other non-Neisseria bacteria.

Therefore, the behavior of the probes toward representative *Neisseria gonorrhoeae* and non-*Neisseria gonorrhoeae* bacteria was determined by hybridization analysis.

EXAMPLE 1

Dot blot analysis of probe hybridization behavior

Dot blot analysis, in accordance with well known procedures, involves immobilizing a nucleic acid or a population of nucleic acids on a filter such as nitrocellulose, nylon, or other derivatized membrane which readily can be obtained commercially, specifically for this purpose. Either DNA or RNA can be easily immobilized on such a filter and subsequently can be probed or tested for hybridization under any of a variety of conditions (i.e., stringencies) with nucleotide sequences or probes of interest. Techniques also are available in which DNA or RNA present in crude (unpurified) cell lysates can be immobilized without first having a purify the nucleic acid in question (e.g. Maniatis, T., Fritsch, E. F. and Sambrook, J., 1982, Molecular Cloning:A Laboratory Manual). This latter approach was found to significantly decrease the amount of effort required to screen for particular nucleotide sequences which may be present in the nucleic acids of any particular organism and, moreover, is advantageously amenable to the mass screening of large numbers of organisms. The probes were end-labeled with radioactive phosphorous 32, using standard procedures. Following hybridization and washing as described above, the hybridization filters were exposed to X-ray film and the intensity of the signal "scored" with respect to control spots of known amount of target material (cells or RNA) visually.

Under stringent conditions, probes whose nucleotide sequences have greater complementarity to the target sequence will exhibit a higher level of hybridization than probes containing less complementarity. For the oligonucleotide probes described herein, hybridization to rRNA targets at 60° C. for 14–16 hours (in a hybridization solution containing 0.9M NaCl, 0.12M Tris-HCl, pH 7.8, 6 mM EDTA, 0.1M KPO4, 0.1% SDS, 0.1% pyrophosphate, 0.002% ficoll, 0.02% BSA, and 0.002% polyvinylpyrrolidone), followed by three 15 minute post-hybridization washes at 60° C. (in 0.03M NaCl, 0.004M Tris-HCl, pH 7.8, 0.2 mM EDTA, and 0.1% SDS) to remove unbound probes, would be sufficiently stringent to produce the levels of specificity demonstrated in Tables 1 and 2.

Tables 3 and 4, illustrate representative results of dot blot hybridization testing of the some 28 strains/isolates of *Neisseria gonorrhoeae*. A small but representative sampling of strains, isolated from different clinical sources, was obtained from the American Type Culture Collection (ATCC). The rest were isolates obtained from various culture collections and patient populations as indicated in Tables 3 and 4. Only results using the *N. gonorrhoeae*-specific probes of the present invention are shown. The various helper probes are not *N. gonorrhoeae*-specific as can be inferred from the sequence comparisons shown in Tables 1 and 2.

The inclusivity behavior of probes 919, 1209, IG700, and IG705 can be summarized as follows: All probes hybridize to (i.e. are fully inclusive for) all *N. gonorrhoeae* tested.

The various helper probes described above were not tested in the hybridization experiments shown in Tables 3 and 4, which were designed to test the inclusivity and exclusivity behavior of the *N. gonorrhoeae*-specific probes. The helper/detection probes are not *N. gonorrhoeae*-specific. By analysis of the available 16S and 23S rRNA sequences it can be predicted with good confidence that they will hybridize to all *N. gonorrhoeae* (and a good many other) bacteria. Such helper probes influence the kinetics and thermodynamics of the hybridization reaction, shifting the distribution of products favorably toward formation of the desired inter-molecular probe/target complexes.

The date shown in Table 3 show that the inclusivity behavior of the probes toward *N. gonorrhoeae* strains is excellent. Because the *N. gonorrhoeae* strains tested (Table 3) were selected as a broad representation of that species, the inclusivity behavior of the probes with respect to additional *N. gonorrhoeae* strains can be predicted to be quite good.

With respect to exclusivity (i.e., hybridization to non-*Neisseria gonorrhoeae*) the probes also behave quite similarly. With the minor exception of probe IG705 (which hybridized weakly to one tested strain of *N. flava* Table 4), none of the probes hybridized to any non-*N. gonorrhoeae* bacterium tested. As is evident in Table 4, lack of hybridization by the probes to *N. meningitidis* was tested most carefully (19 strains). *N. meningitidis* is the closest genetic relative of *N. gonorrhoeae* known (by DNA hybridization studies). *N. meningitidis* also is known to be found occasionally in samples which commonly are tested for *N. gonorrhoeae*. For both of these reasons, the ability of the probes to discriminate between *N. gonorrhoeae* and *N. meningitidis* is deemed to be quite important.

Except as noted above, none of the probes hybridize to any other Neisseria species or any non-Neisseria bacterium tested.

The discovery that probes could be generated with the extraordinary inclusivity and exclusivity characteristics of those of the present invention with respect to *Neisseria gonorrhoeae* was unpredictable and unexpected.

Description and Utility of the Probe Sets

In addition to the *N. gonorrhoeae*-specific probes 919, 1209, IG700 and IG705 described above, a number of probe sets including these probes plus other helper probes are described. In the simplest cases the helper probes do no more than increase the hybridization efficiency of the aforementioned *N. gonorrhoeae*-specific probes by assisting those probes in gaining access to their target sequences. The following sets of probes having this property of improved hybridization are as follows:

| Probe Set | *N. gonorrhoeae*-specific probe | Helper Probe(s) |
|---|---|---|
| 1 | 919 | 1116, 1117 |
| 2 | 1209 | 1208 |
| 3 | IG700 | IG706 |
| 4 | IG705 | 1750 |

In addition to structure-opening functions, such "helper" probes may also incorporate other functions. For example, in certain sandwich-type hybridization assay formats two probes are required to generate a positive signal. One, usually the target-organism-specific probe is modified in such a way that it not only hybridizes to the target molecule but simultaneously or subsequently also can be captured out of the sample matrix onto a solid support surface. The other probe of the set also must hybridize to the target and, in addition, is modified to contain a detectable ligand. For example, probes 1116 and 1117 have significant value as companion probes to probe 919 for use in any of a variety of dual probe, sandwich-type hybridization assay formats (e.g. the homopolymer capture, dual probe, liquid hybridization format described in U.S. Ser. Nos. 277,579; 169,646, or 233,683). In such an application, probe 919, or a derivative thereof would be modified at its 3' terminus to contain a tract of deoxyadenosine (dA) residues ca. 20–200 residues long. This would be used to "capture" the target rRNA (following liquid hybridization) from the test sample onto a solid support (e.g., beads, plastic surface, filter, etc.) which had been suitably derivatized with poly-deoxythymidine (dT) for this purpose. Probes 1116 and/or 1117 (or derivatives thereof) would be used as the detection probe and would be derivatized by some detectable ligand (e.g. 32-P, fluorescein, biotin, etc.) The modified cytosine residues indicated in Table 1 are useful as a convenient means of attaching such a ligand. Detection of the presence of the target nucleic acid in a test sample then is indicated by the capture of the detection ligand onto the solid surface through the series of hybridization interactions:

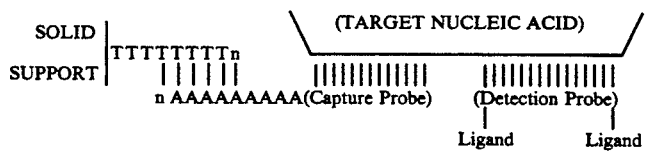

The detection probe can only become bound to the solid support if the target nucleic acid is present in the test sample.

The physical proximity of the target sites of the capture and detection probes minimizes the chance that ribonuclease present in some test samples might negatively impact the test result by severing the target rRNA molecule between these target sites. Probes 1116 and 1117 also are designed to enhance the hybridization of probe 919 by opening up the secondary structure which involves the target region of the latter.

Likewise, the other described "helper" probes enhance the behavior of the *N. gonorrhoeae*-specific probes of their respective sets.

One further useful probe set can be defined based on the probe sets described above. This is a combination of probe set 3 and 4, and is designated probe set 5.

| Probe Set | *N. gonorrhoeae*-specific probe | Helper Probe(s) |
|---|---|---|
| 5 | IG700, IG705 | IG706, 1750 |

In the dual probe, sandwich hybridization assay format described above, the probes of probe set 5 could be used to advantage in several ways. for example, both IG700 and IG705could be used as specific capture probes in order to enhance the efficiency of hybridization to the *N. gonorrhoeae* 23S rRNA target molecules. In this case the helper probes could still be used as non-specific detection probes and also as helpers to open up the target structure. This, in principle, would increase the signal obtainable from the assay by capturing more 23S target molecules than would be captured by using a single capture probe.

Another possible variation which would add "robustness" to the assay would be to use IG700 as the capture probe and IG705 as the detection probe (or vice versa). Unmodified helper probes then would serve primarily in their structure opening capacity. But in this format both the capture and detection probes would advantageously be specific for the target nucleic acid. This makes it less likely that a false positive hybridization signal would be generated, for example, by low level hybridization of a non-specific detection probe to the target nucleic acid. In general, such a dual specific probe assay is preferably to a specific/non-specific one and can often be advantageously used to increase both hybridization efficiency and specifity of the assay.

While the description of the invention has been made with reference to detecting rRNA, it will be readily understood that the probes described herein and probes complementary to those described herein also will be useful for the detection of the genes (DNA) which specify the rRNA (i.e., "rDNA") and, accordingly, such probes are to be deemed equivalents to the described probes and encompassed within the spirit and scope to the present invention and the appended claims.

TABLE 1

NEISSERIA GONORRHOEAE 16S rRNA CORE AND PROBE SEQUENCE INFORMATION

A) The Probe 919 Target Region.

Position # (*E. coli*) 401 — 445

| Organism | Sequence |
|---|---|
| *Escherichia coli* | CGCGUGUAUGAAGAAGGCCUUCGGGUUGUAAAGUACUUUCAGCGG |
| *Proteus vulgaris* | CGCGUGUAUGAAGAAGGCCUUAGGGUUGUAAAGUACUUUCAGCGG |
| *Vibrio harveyi* | CGCGUGUGUGAAGAAGGCCUUCGGGUUGUAAAGCACUUUCAGUCG |
| *Pseudomonas testosteroni* | CGCGUGCAGGAUGAAGGCCCUCGGGUUGUAAACUGCUUUUGUACG |
| *Neisseria gonorrhoeae* 9793 | NGCGUGUCUGAAGAAGGCCUUCGGGUUGUAAAGGACUUUUGUCAG |
| *Neisseria gonorrhoeae* 19424 | -----------------N-------------------------- |
| *Neisseria meningitidis* 13090 | C------------------------------------------- |
| *Neisseria meningitidis* 13102 | C------------------------------------------- |
| *Neisseria meningitidis* 13113 | C----------------N-------------------------- |
| *Neisseria lactamica* 23970 | C----------------N----------------N------G- |

Probe 1117  T c GCACAGACTTCTTCCGGAAGCCCAACATTTCCTGAAAACAc-5'

Position # (*E. coli*) 446 458 477 490

| Organism | Sequence |
|---|---|
| *Escherichia coli* | GGAGGAAGGGAGUAAAGUUAAUACCUUUGCUCAUUGACGUUACCC |
| *Proteus vulgaris* | GGAGGAAGGUGAUAAAGUUAAUACCUUUGUCAAUUGACGUUACCC |
| *Vibrio harveyi* | UGAGGAAGGUAGUGNAGUUAAUAGCUGCAUUAUUUGACGUUAGCG |
| *Pseudomonas testosteroni* | GAACGAAAAGCCUGGGGCUAAUAUCCCCGGGUCAUGACGGUACCG |
| *Neisseria gonorrhoeae* 9793 | GGAAGAAAAGGCCGUUGCCAAUAUCGGCGGCCGAUGACGGUACCU |
| *Neisseria gonorrhoeae* 19424 | -----------U-----------------U-------------- |
| *Neisseria gonorrhoeae* 8375 | -----------U-------------------------------- |
| *Neisseria meningitidis* 13090 | -----------U-----U------A-----U-------------- |
| *Neisseria meningitidis* 13113 | -----------U-----N------A-----U-------------- |
| *Neisseria meningitidis* 13102 | -----------NN----U------A-----U-------------- |
| *Neisseria lactamica* 23970 | -----------U--GG-UU----C-CU----U------------C |

TABLE 1-continued
NEISSERIA GONORRHOEAE 16S rRNA CORE AND PROBE SEQUENCE INFORMATION

| | |
|---|---|
| Core variation | CGUUGCCAAUAUCGGCGGCC |
| Probe 919 | Tc TTCCGGCAACGGTTATAGCCGCCGGCTAc-5' |
| Probe 1114 | Tc TTTCCGGCAACGGTTATAGCCGCCGGCTACTc-5' |
| Probe 1115 | Tc CTTTTCCGGCAACGGTTATAGCCGCCGGCTACTGCCc-5' |

| Position # (E. coli) | 491                                                         541 |
|---|---|
| Escherichia coli | GCAGAAGAAGCACCGGCUAACUCCGUGCCAGCAGCCGCGGUAAUACGGAGG |
| Proteus vulgaris | GCAGAAGAAGCACCGGCUAACUCCGUGCCAGCAGCCGCGGUAAUACGGAGG |
| Vibrio harveyi | ACNGAAGAAGCACCGGCUAACUCCGUGCCAGCAGCCGCGGUAAUACGGAGN |
| Pseudomonas testoseroni | UAAGAAUAAGCACCGGCUAACUACGUGCCAGCAGCCGCGGUAAUACGUAGG |
| Neisseria gonorrhoeae 9793 | NAAGAAUAAGCACCGGCUAACUACGUGCCAGCAGCCNCGNNNAUACGUAGG |
| Neisseria gonorrhoeae 12424 | G--------------------------------------------------- |
| Neisseria meningitidis 13090 | G--------------------------------------------------- |
| Neisseria meningitidis C13102 | G----N----------------------------------------------- |
| Neisseria meningitidis 13113 | G----N----------------------------------------------- |
| Neisseria lactamica 23970 | G----------------------------------------G--GU--------- |

| Probe 1116 | Tc TCTTATTCGTGGCCGATTGATGCACGGTCGTCGACGCCATTATGCc-5' |
|---|---|

B) The Probe 1209 Target Region.

| Position # (E. coli) | 979                                                 1017 |
|---|---|
| Escherichia coli | CCUUACCUGGUCUUGACAUCCACGGAAGUUUUCAGAGAU |
| Proteus vulgaris | CCUUACCUACUCUUGACAUCCAGCGAAUCCUUUAGA |
| Vibrio harveyi | CCU-ACCUACUCUUGACAUCCAGGAAACUUUCCAGA |
| Pseudomonas testosteroni | CCUUACCCACCUUUGACAUGGCAGGAACUUACCAGA |
| Neisseria gonorrhoeae 9793 | CCUUACCUGGUUUUGACAUGUGCGGAAUCCUCCGGA |
| Neisseria gonorrhoeae 19424 | --------N------------------------------ |
| Neisseria gonorrhoeae 8375 | -------------------------------------- |
| Neisseria gonorrhoeae 2013 | -------------------------------------- |
| Neisseria meningitidis 13090 | -----------C----------A-------------- |
| Neisseria meningitidis gts1349 | --NN-------C----------A----------A-- |
| Neisseria meningitidis gts1346 | -----------C----------A-------------- |
| Neisseria lactamica 23970 | -------C--------------A-------------- |

| | |
|---|---|
| Core variation | Uuugacaugu G |
| Probe 1209 | TGGACCAAAACTGTACACGCCTTAGGAG-5' |

| Position # (E. coli) | 1018                                                   1057 |
|---|---|
| Escherichia coli | GAGAAUGUGCCUU--CGGGAACCGUGAGACAGGUGCUGCAUG |
| Proteus vulgaris | AGAGGAGUGCCUU--CGGGAACCGUGAGACAGGUGCUGCAUG |
| Vibrio harveyi | GGAUUNGUGCCU---CGGGAACCGUGAGACAGGUGCUGCAUG |
| Pseudomonas testosteroni | GGUUUGGUGCUCGAAAGAGAACCUGCACACAGGUGCUGCAUG |
| Neisseria gonorrhoeae 9793 | GGAGGNGUGCCUU--CGGGAGCCGUAACACAGGUGCUGCAUG |
| Neisseria gonorrhoeae 8375 | -----A----------------------------------- |
| Neisseria gonorrhoeae 2013 | ----NA----------------------------------- |
| Neisseria meningitidis gts1349 | ----N-N---------------------------------- |
| Neisseria meningitidis gts1346 | ----N---------------N-------------------- |
| Neisseria lactamica 23970 | --G--N----------------------------------- |

| Probe 1208 | Tc CACGGAA--GCCCTCGGCATTGTGTCCACGc-5' |
|---|---|

TABLE 2

NEISSERIA GONORRHOEAE 23S rRNA CORE AND PROBE SEQUENCE INFORMATION

A) The Probe IG700 Target Region.

| | |
|---|---|
| Position # (E. coli) | 50                                    85 |
| Escherichia coli | UGAAGGACGUGCUAAUCUGCGAUAAGCGUCGGUAAG |
| Neisseria gonorrhoeae 9793 | CGAAGGACGUGUAAGCCUGCGAAAAGCGCCGGGGAG |
| Neisseria meningitidis 13090 | ------------------------------------ |
| | |
| Probe IG706 | CTGCACATTCGGACGCTTTTCGCGCCCC-5' |
| | |
| Position # (E. coli) | 86                                     119 |
| Escherichia coli | GUGAUAUGAACCGUUAUAACCGGCGAUUUCCGAA |
| Neisseria gonorrhoeae 9793 | NUGGCAAUAAAGCUAUGAUUCCGCGAUGUCCGAA |
| Neisseria meningitidis 13090 | C-----------A-----C-------------- |
| | |
| Core variation | U a u g a u C |
| Probe IG700 | CGTTATTTCGATACTAAGGCGCTACAGG-5' |

B) The Probe IG705 Target Region.

| | |
|---|---|
| Position # (E. coli) | 120                                      154 |
| Escherichia coli | GGGAAACCCAGUGUGUUUCGACACACUAUCAUU |
| Neisseria gonorrhoeae 9793 | GGGAAACCCACUGCAUUCU-GUGCAGUAUCCUA |
| Neisseria meningitidis 13090 | --------------------------------- |
| | |
| Probe 1750 | TTGGGTGACGTAAGA-CACGTCATAGGAT-5' |
| | |
| Position # (E. coli) | 155                                     186 |
| Escherichia coli | AACUGAAUCCAUAGG-UUAAUGAGGCGAACCGG |
| Neisseria gonorrhoeae 9793 | AGUUGAAUACAUAGGCUUAGAGAAGCGAACCCG |
| Neisseria meningitidis 13090 | --------------A------------------ |
| | |
| Core variation | G |
| Probe IG705 | CAACTTATGTATCCGAATCTCTTCGCTT-5' |

TABLE 3

INCLUSIVITY DOT BLOT HYBRIDIZATION DATA

| | | | PROBE HYBRIDIZATION INDEX | | | |
|---|---|---|---|---|---|---|
| GENUS.SPECIES | STRAIN | SOURCE | 919 | 1209 | IG700 | IG705 |
| Neisseria gonorrhoeae | 9793 | (1) | +++ | +++ | +++ | ++ |
| Neisseria gonorrhoeae | 27632 | (1) | +++ | +++ | +++ | ++ |
| Neisseria gonorrhoeae | 27633 | (1) | +++ | +++ | +++ | ++ |
| Neisseria gonorrhoeae | 31426 | (1) | +++ | +++ | +++ | ++ |
| Neisseria gonorrhoeae | 19424 | (1) | +++ | +++ | +++ | ++ |
| Neisseria gonorrhoeae | 27628 | (1) | +++ | +++ | +++ | ++ |
| Neisseria gonorrhoeae | 44 | (2) | +++ | +++ | +++ | ++ |
| Neisseria gonorrhoeae | 042 | (2) | +++ | +++ | +++ | ++ |
| Neisseria gonorrhoeae | H02 | (2) | +++ | +++ | +++ | ++ |
| Neisseria gonorrhoeae | Syv17 | (2) | +++ | +++ | +++ | ++ |
| Neisseria gonorrhoeae | 27629 | (1) | +++ | +++ | +++ | ++ |
| Neisseria gonorrhoeae | 27630 | (1) | +++ | +++ | +++ | ++ |
| Neisseria gonorrhoeae | 27631 | (1) | +++ | +++ | +++ | ++ |
| Neisseria gonorrhoeae | 10896 | (1) | +++ | +++ | +++ | ++ |
| Neisseria gonorrhoeaa | GC-18 | (4) | +++ | +++ | +++ | ++ |
| Neisseria gonorrhoeae | GC-17 | (4) | +++ | +++ | +++ | ++ |
| Neisseria gonorrhoeae | GC-24 | (4) | +++ | +++ | +++ | ++ |
| Neisseria gonorrhoeae | GC-23 | (4) | +++ | +++ | +++ | ++ |
| Neisseria gonorrhoeae | GC-16 | (4) | +++ | +++ | +++ | ++ |
| Neisseria gonorrhoeae | GC-20 | (4) | +++ | +++ | +++ | ++ |
| Neisseria gonorrhoeae | GC-22 | (4) | +++ | +++ | +++ | ++ |
| Neisseria gonorrhoeae | GC-19 | (4) | +++ | +++ | +++ | ++ |
| Neisseria gonorrhoeae | G14FA171 | (5) | +++ | +++ | +++ | ++ |
| Neisseria gonorrhoeae | 405 | (3) | +++ | +++ | +++ | ++ |
| Neisseria gonorrhoeae | 410 | (3) | +++ | +++ | +++ | ++ |
| Neisseria gonorrhoeae | 413 | (3) | +++ | +++ | +++ | ++ |
| Neisseria gonorrhoeae | 444 | (3) | +++ | +++ | +++ | ++ |

TABLE 3-continued
INCLUSIVITY DOT BLOT HYBRIDIZATION DATA

| GENUS.SPECIES | STRAIN | SOURCE | PROBE HYBRIDIZATION INDEX | | | |
|---|---|---|---|---|---|---|
| | | | 919 | 1209 | IG700 | IG705 |
| *Neisseria gonorrhoeae* | 446 | (3) | +++ | +++ | +++ | ++ |

HYBRIDIZATION INDEX
+++ = Positive control level of hybridization
++ = Strong hybridization
− = No detectable hybridization
SOURCE KEY:
(1) American Type Culture Collection, Rockville, MD
(2) Clinical isolates - Dr. Michael Spence, Hahnemann University, Philadelphia, PA
(3) Clinical isolates - Dr. M. Haines, University of Miami, Miami, FL
(4) Clinical isolates - Massachusetts State Health Laboratory, Jamaica Plain, MA
(5) Clinical isolates - Jan Cannon, University of North Carolina, Chapel Hill, NC

TABLE 4
EXCLUSIVITY DOT BLOT HYBRIDIZATION DATA

A) Hybridization vs. non-gonorrhoeae Neisseria.

| GENUS.SPECIES.SEROTYPE | STRAIN | SOURCE | PROBE HYBRIDIZATION INDEX | | | |
|---|---|---|---|---|---|---|
| | | | 919 | 1209 | IG700 | IG705 |
| *Neisseria meningitidis* | | 13077 | (1) | − | − | − | − |
| *Neisseria meningitidis* | | 13090 | (1) | − | − | − | − |
| *Neisseria meningitidis* | | 13102 | (1) | − | − | − | − |
| *Neisseria meningitidis* | | 13113 | (1) | − | − | − | − |
| *Neisseria meningitidis* | | GC-1 | (4) | − | − | − | − |
| *Neisseria meningitidis* | A | M1 7880 | (6) | − | − | − | − |
| *Neisseria meningitidis* | C | M2 1381 | (6) | − | − | − | − |
| *Neisseria meningitidis* | B | 1126 | (3) | − | − | − | − |
| *Neisseria meningitidis* | B | 1058 | (3) | − | − | − | − |
| *Neisseria meningitidis* | B | 14 | (3) | − | − | − | − |
| *Neisseria meningitidis* | Non-A-D,X-Z,W-135 | | (3) | − | − | − | − |
| *Neisseria meningitidis* | B | 116 | (2) | − | − | − | − |
| *Neisseria meningitidis* | B | 2341 | (2) | − | − | − | − |
| *Neisseria meningitidis* | X | 2733 | (2) | − | − | − | − |
| *Neisseria meningitidis* | Y | 140 | (2) | − | − | − | − |
| *Neisseria meningitidis* | B | 131 | (2) | − | − | − | − |
| *Neisseria meningitidis* | SR | 174 | (2) | − | − | − | − |
| *Neisseria meningitidis* | W135 | 2213 | (2) | − | − | − | − |
| *Neisseria meningitidis* | B | 366 | (3) | − | − | − | − |
| *Neisseria cinerea* | | 14685 | (1) | − | − | − | − |
| *Neisseria denitrificans* | | 14686 | (1) | − | − | − | − |
| *Neisseria elongata* | | 25925 | (1) | − | − | − | − |
| *Neisseria flava* | | C11CTM1.5 | (4) | − | − | − | ++ |
| *Neisseria flavescens* | | 13120 | (1) | − | − | − | − |
| *Neisseria lactamica* | | 23970 | (1) | − | − | − | − |
| *Neisseria lactamica* | | C1 | (5) | − | − | − | − |
| *Neisseria mucosa* | | 19696 | (1) | − | − | − | − |
| *Neisseria polysaccharea* | | 36088 | (1) | − | − | − | − |
| *Neisseria sicca* | | 30016 | (1) | − | − | − | − |
| *Neisseria subflava* | | 14799 | (1) | − | − | − | − |

HYBRIDIZATION INDEX
+++ = Positive control level of hybridization
++ = Strong hybridization
− = No detectable hybridization
SOURCE KEY:
(1) American Type Culture Collection, Rockville, MD
(2) Clinical isolates - Dr. Lai-King Ng, Laboratory Centre for Disease Control, Ottowa, Ontario, Canada
(3) Clinical isolates - Massachusetts State Health Laboratory, Jamaica Plain, MA
(4) Clinical isolates - Joan Knapp, Centers for Disease Control, Atlanta, GA
(5) Clinical isolates - Jan Cannon, University of North Carolina, Chapel Hill, NC
(6) Clinical isolates - M. Griffis, University of San Francisco, San Francisco, CA B) Hybridization vs. non-Neisseria.

| GENUS.SPECIES | STRAIN | SOURCE | PROBE HYBRIDIZATION INDEX | | | |
|---|---|---|---|---|---|---|
| | | | 919 | 1209 | IG700 | IG705 |
| *Alcaligines faecalis* | 8750 | (1) | − | − | − | − |
| *Branhamella catarrhalis* | 8176 | (1) | − | − | − | − |
| *Chromobacterium violaceum* | 12472 | (1) | − | − | − | − |
| *Eikenella corrodens* | 23834 | (1) | − | − | − | − |
| *Kingella kingae* | 23330 | (1) | − | − | − | − |
| *Kingella denitrificans* | 33394 | (1) | − | − | − | − |
| *Moraxella osloensis* | 19962 | (1) | − | − | − | − |
| *Oligella urethralis* | 17960 | (1) | − | − | − | − |
| *Pseudomonas cepacia* | 13945 | (1) | − | − | − | − |
| *Pseudomonas testosteroni* | 11996 | (1) | − | − | − | − |
| *Vitreoscilla stercoraria* | VT1 | (3) | − | − | − | − |
| *Acinetobacter calcoaceticus* | 19606 | (1) | − | − | − | − |

TABLE 4-continued

| EXCLUSIVITY DOT BLOT HYBRIDIZATION DATA | | | | | | |
|---|---|---|---|---|---|---|
| Citrobacter freundii | 8090 | (1) | — | — | — | — |
| Escherichia coli | 2 | (2) | — | — | — | — |
| Klebsiella pneumoniae | 13883 | (1) | — | — | — | — |
| Morganella morganii | 25830 | (1) | — | — | — | — |
| Proteus mirabilis | 29906 | (1) | — | — | — | — |
| Pseudomonas aeruginosa | 27853 | (1) | — | — | — | — |
| Vibrio parahemolyticus | 17802 | (1) | — | — | — | — |
| Yersinia enterocolitica | 9610 | (1) | — | — | — | — |
| Bacillus subtilis | 23059 | (1) | — | — | — | — |
| Clostridium perfringens | 13124 | (1) | — | — | — | — |
| Lactobacillus plantarum | 8014 | (1) | — | — | — | — |
| Staphylococcus aureus | 25923 | (1) | — | — | — | — |
| Bacteroides fragilis | 25285 | (1) | — | — | — | — |
| Human/CaSKi | | | — | — | — | — |
| Candida albicans | 18804 | (1) | — | — | — | — |

HYBRIDIZATION INDEX
+ + + = Positive control level of hybridization
+ + = Strong hybridization
— = No detectable hybridization
SOURCE KEY:
(1) American Type Culture Collection, Rockville, MD
(2) Grace Thorne, The Children's Hospital, Boston
(3) W. R. Strohl, The Ohio State University, Columbus, OH

What is claimed is:

1. A method of detecting the presence of *Neisseria gonorrhoeae* in a sample comprising:
   a) contacting said sample with a nucleic acid probe which preferentially hybridizes to rRNA or rDNA of *Neisseria gonorrhoeae* over rRNA or rDNA of non-Neisseria bacteria, wherein said probe is complementary to a region of the *Neisseria gonorrhoeae* 16S rRNA selected from the group of regions consisting of the region 455 through 477 and the region 983 through 1010, and the region of the *Neisseria gonorrhoeae* 23S rRNA selected from the group of regions consisting of the region 89 to 116 and the region 156 to 182;
   b) imposing hybridization conditions on said sample and the nucleic acid probe to allow the nucleic acid probe to hybridize to the rRNA or rDNA of *Neisseria gonorrhoeae*, if present in said sample, to form hybridized nucleic acid complexes, under conditions which do not allow said nucleic acid probe to form stable hybridized nucleic acid complexes with non-Neisseria rRNA or rDNA; and
   c) detecting said hybridized nucleic acid complexes as an indication of the presence of said *Neisseria gonorrhoeae* in said sample.

2. The method of claim 1, wherein said probe does not hybridize under said hybridization conditions to rRNA or rDNA of *Acinetobacter calcoaceticus, Bacteroides fragilis, Branhamella catarrhalis, Citrobacter freundii, Enterobacter agglomerans, Escherichia coli, Gardnerella vaginalis, Haemophilus ducreyii, Haemophilus influenzae, Klebsiella pneumoniae, Kingella kingae, Kingella denitrificans, Lactobacillus acidophilus, Mobiluncus mulieris, Moraxella osloensis, Morganella morganii, Neisseria cinerea, Neisseria denitrificans, Neisseria elongata, Neisseria flavescens, Neisseria lactamica, Neisseria meningitidis A, Neisseria meningitidis B, Neisseria meningitidis C, Neisseria meningitidis D, Neisseria mucosa, Neisseria subflava, Pseudomonas aeruginosa, Salmonella arizona, Salmonella typhimurium, Shigella flexnerii, Staphylococcus aureus, Streptococcus agalactiae* and *Veillonella parvula*.

3. The method of claim 1, wherein said nucleic acid probe consists essentially of any one of 16S rRNA probes 919 or 1209, or 23S rRNA probes IG700 or IG705, or their complementary nucleotide sequences.

4. The method of claim 1 wherein said contacting step comprises contacting said sample with two nucleic acid probes, one of which is probe 919 or its complementary sequence and the other of which is selected from the group of probe 1116, probe 1117 and their complementary sequences.

5. The method of claim 1 wherein said contacting step comprises contacting said sample with two nucleic acid probes, one of which is probe 1209 or its complementary sequence and the other of which is probe 1208 or its complementary sequence.

6. The method of claim 1 wherein said contacting step comprises contacting said sample with two nucleic acid probes, one of which is probe IG700 or its complementary sequence and the other of which is probe IG706 or its complementary sequence.

7. The method of claim 1 wherein said contacting step comprises contacting said sample with two nucleic acid probes, one of which is probe IG705 or its complementary sequence and the other of which is probe 1750 or its complementary sequence.

8. The method of claim 1 wherein said contacting step comprises contacting said sample with two nucleic acid probes, one of which is probe IG700 or its complementary sequence and the other of which is probe IG705 or its complementary sequence.

* * * * *